(12) United States Patent
Taberna et al.

(10) Patent No.: US 10,865,371 B2
(45) Date of Patent: Dec. 15, 2020

(54) LARGE SCALE MIXOTROPHIC PRODUCTION SYSTEMS

(71) Applicant: HELIAE DEVELOPMENT LLC, Gilbert, AZ (US)

(72) Inventors: Eneko Ganuza Taberna, Phoenix, AZ (US); Thomas Adame, Chandler, AZ (US); Anna Lee Tonkovich, Gilbert, AZ (US); Adriano Galvez, Gilbert, AZ (US); Timothy Sullivan, Gilbert, AZ (US)

(73) Assignee: Heliae Development LLC, Gilbert, AZ (US)

( * ) Notice: Subject to any disclaimer, the term of this patent is extended or adjusted under 35 U.S.C. 154(b) by 296 days.

(21) Appl. No.: 14/822,716

(22) Filed: Aug. 10, 2015

(65) Prior Publication Data

US 2015/0344830 A1    Dec. 3, 2015

Related U.S. Application Data

(63) Continuation of application No. PCT/US2014/028604, filed on Mar. 14, 2014.

(60) Provisional application No. 61/798,969, filed on Mar. 15, 2013, provisional application No. 61/919,008, filed on Dec. 20, 2013.

(51) Int. Cl.
    *C12M 1/00*    (2006.01)
    *C12M 1/34*    (2006.01)
    *C12M 1/06*    (2006.01)
    *C12M 1/02*    (2006.01)
    *C12M 3/00*    (2006.01)

(52) U.S. Cl.
    CPC ............ *C12M 21/02* (2013.01); *C12M 23/18* (2013.01); *C12M 23/34* (2013.01); *C12M 23/38* (2013.01); *C12M 27/06* (2013.01); *C12M 41/24* (2013.01); *C12M 41/26* (2013.01)

(58) Field of Classification Search
    CPC ...................................................... C12M 21/02
    USPC ...................................................... 435/292.1
    See application file for complete search history.

(56) References Cited

U.S. PATENT DOCUMENTS

| 4,005,546 | A | 2/1977 | Oswald |
| 4,452,227 | A | 6/1984 | Lowrey, III |
| 4,510,920 | A | 4/1985 | Walmet |
| 4,643,830 | A | 2/1987 | Reid |

(Continued)

FOREIGN PATENT DOCUMENTS

| JP | 50011466 | 5/1975 |
| JP | 2011254724 | 12/2011 |

(Continued)

OTHER PUBLICATIONS

Parker, Air-lift pumps and other aeration techniques, 1983, Southern Cooperative Bulletin, vol. 290 (Year: 1983).*

(Continued)

*Primary Examiner* — Holly Kipouros
(74) *Attorney, Agent, or Firm* — Heliae Development LLC; Veronica-Adele Cao; Adam Lunceford

(57) ABSTRACT

Bioreactor systems for culturing mixotrophic microorganisms in open cultures on a large scale are disclosed herein. Embodiments of the system comprise organic carbon delivery systems and submersible thrusters suspended on adjustable support structures.

17 Claims, 8 Drawing Sheets

(56) References Cited

U.S. PATENT DOCUMENTS

| | | | |
|---|---|---|---|
| 5,121,708 A * | 6/1992 | Nuttle | A01G 31/02 |
| | | | 119/200 |
| 6,659,044 B2 | 12/2003 | Salinas | |
| 6,852,225 B1 | 2/2005 | Oswald | |
| 8,017,377 B1 | 9/2011 | Much | |
| 8,535,532 B2 | 9/2013 | Ott | |
| 8,642,325 B1 | 2/2014 | Benjauthrit | |
| 2007/0264708 A1 | 11/2007 | Bayless | |
| 2008/0311646 A1 | 12/2008 | Cong | |
| 2010/0068801 A1 * | 3/2010 | Woods | C12M 21/02 |
| | | | 435/292.1 |
| 2010/0099170 A1 | 4/2010 | Aswani | |
| 2010/0216218 A1 | 8/2010 | Huang | |
| 2010/0237009 A1 | 9/2010 | Horst | |
| 2010/0260618 A1 | 10/2010 | Parsheh | |
| 2010/0264094 A1 | 10/2010 | Schwartz | |
| 2011/0294196 A1 | 12/2011 | Machin | |
| 2011/0318816 A1 | 12/2011 | Hazlebeck | |
| 2012/0088296 A1 | 4/2012 | Vargas | |
| 2012/0171753 A1 * | 7/2012 | Ivry | B01F 13/0015 |
| | | | 435/257.3 |
| 2012/0208254 A1 | 8/2012 | Smith | |
| 2012/0272574 A1 * | 11/2012 | Parsheh | A01G 33/00 |
| | | | 47/62 R |
| 2012/0295336 A1 * | 11/2012 | Hazlebeck | C12N 1/12 |
| | | | 435/257.1 |
| 2013/0042522 A1 | 2/2013 | Delobel | |
| 2013/0095544 A1 | 4/2013 | Berlowitz | |
| 2013/0164834 A1 | 6/2013 | Licamele | |
| 2013/0269244 A1 | 10/2013 | Jovine | |

FOREIGN PATENT DOCUMENTS

| | | |
|---|---|---|
| WO | 2009090521 | 7/2009 |
| WO | 2009134114 | 11/2009 |
| WO | 2010077638 | 7/2010 |
| WO | 2012109375 | 8/2012 |
| WO | 2012166883 | 12/2012 |
| WO | 2011065445 | 4/2013 |
| WO | 2013186626 | 12/2013 |

OTHER PUBLICATIONS

Xylem. Flygt compact mixers. Accessed online Mar. 13, 2014 at htttp://www.flygt.com/en-us/Mixing/Products/F;ygt-compact-mixers-4600-series/Documents/1103_Master_Lo.pdf.

Moazami, et al, "Large-Scale Biodiesel production using microalage biomass of Nannochloropsis", Biomass and Bioenergy, 2012, vol. 39, 449-453, pp. 450, 451.

Sanchez, et al, "Culture aspects of Isochrysis galbana for biodiesel production", Applied Energy, 2013, vol. 101, pp. 192-197. p. 193, Published online Apr. 16, 2012.

Chiaramonti, et al, "Review of energy balance in raceway ponds for microalage cultivation: Rethinking a traditional system is possible", Applied Energy. 2013, vol. 102, pp. 101-111. Published online Sep. 11, 2012.

* cited by examiner

LARGE SCALE MIXOTROPHIC PRODUCTION SYSTEMS

CROSS REFERENCE TO RELATED APPLICATIONS

This application claims the benefit of PCT Application No. PCT/US2014/028604, filed Mar. 14, 2014, entitled Large Scale Mixotrophic Production Systems, U.S. Provisional Application No. 61/798,969, filed Mar. 15, 2013, entitled Mixotrophy Systems and Methods, and U.S. Provisional Application No. 61/919,008, filed Dec. 20, 2013, entitled Large Scale Mixotrophic Production Systems, the entire contents of which are hereby incorporated by reference.

BACKGROUND

The large scale culturing of microorganisms has been established primarily in two categories, phototrophy and heterotrophy. Phototrophy comprises culture conditions in which the microorganisms utilize light as an energy source and inorganic carbon (e.g., carbon dioxide, bi-carbonate) for photosynthetic activity, which facilitates growth of the microorganism and the production of oxygen. Heterotrophy comprises culture conditions in which microorganisms utilize organic carbon as an energy and carbon source to facilitate growth of the microorganism and production of carbon dioxide. Phototrophy performed at a large scale in open ponds is conventionally performed in non-axenic conditions, but large scale heterotrophy is conventionally performed in the axenic conditions of closed industrial fermenters.

A third category of microorganism culturing known as mixotrophy may also be used when the microorganism has the capability to use both light and organic carbon as the energy source, and organic and inorganic carbon as the carbon source. Mixotrophy may be performed in closed axenic conditions, but may also be performed in lower cost open non-axenic conditions. Mixotrophy provides the potential for an increased growth rate compared to phototrophic cultures and reduced capital costs compared to heterotrophic cultures. Additionally, the use of light in mixotrophy allows for a more diverse product profile to be produced (e.g., pigments, carotenoids) than may be produced in heterotrophic cultures which do not receive any light.

In the prior art, mixotrophy has largely been performed at laboratory or bench top scale, and not in large scale commercial production settings. The laboratory scale uses simple bioreactor systems, such as flasks and bubble columns, at small experimental culture volumes. The information coming out of such laboratory scale bioreactors is limited in its usefulness to industry, as a flask cannot be easily scaled up to produce commercial quantities of microorganisms. Additionally, at the small culture volumes of laboratory and bench top scale it is very easy to control the culture conditions, such as pH, temperature, dissolved gas content, and contamination. As the volume increases to commercial scale, the bioreactor system and microorganism culture faces new challenges not present at the laboratory scale.

The existing large scale production systems for phototrophic and heterotrophic cultures may be used for mixotrophy, but do not take full advantage of the mixotrophic culture conditions to produce an optimal yield or to culture large volumes of mixotrophic microorganisms in the most efficient manner. Large scale ponds used for phototrophic cultures are limited to shallow culture depths to allow light to penetrate the aqueous culture and be available to the microorganisms. Such shallow culture depths result in an inefficient use of land as the volume to surface area ratio is low, and thus the yield of microorganisms and yield of microorganism produced products per surface area of land are not optimized. Large scale fermenters used for heterotrophic culturing require high capital costs due to the materials needed to make the large sealed vessels, and mechanical mixing to properly distribute the gases and organic carbon. The high capital cost of sealed fermenters reduces the margins for profit, and the use of mechanical mixing may produce harmful shear stress for some species of microorganisms. Wastewater treatment systems using microalgae in various stages of treatment utilize large open ponds with a typical depth between 1 and 10 meters, but the systems are designed for optimization of water treatment and not microorganism production, and thus do not facilitate high culture densities which results in low production yields of microorganisms.

To capitalize on the production ability and versatile product profile of mixotrophic microorganisms, a high volume large scale production system specific to the mixotrophic culture methods and conditions is needed that improves on existing deficiencies of large scale phototrophic, heterotrophic, and wastewater systems, and addresses the challenges not faced in bench top scale mixotrophic cultures. Therefore, there is a need in the art for a large scale mixotrophic production system for the efficient production of large volumes of mixotrophic microorganisms.

SUMMARY

Described herein are systems for culturing mixotrophic microorganisms on a large scale. Also described are multifunctional embodiments of a turning vane to provide guidance for fluid flow and other functions such as heat exchange, nutrient delivery, gas delivery, organic carbon delivery, delivery of light, and parameter measurement by sensors.

In one embodiment of the invention, a mixotrophic bioreactor system comprises: at least one lit portion of the bioreactor system configured to contain a culture of mixotrophic microorganisms in an aqueous culture medium in an inner volume and expose the culture of mixotrophic microorganisms in the inner volume to at least some light from a light source; at least one dark portion of the bioreactor system in fluid communication with the at least one lit portion, the at least one dark portion configured to contain the culture of mixotrophic microorganisms in an aqueous culture medium in an inner volume in the absence of light; at least one organic carbon supply device configured to supply organic carbon to a culture of mixotrophic microorganisms; and a circulation system configured to circulate the culture of mixotrophic microorganisms between the at least one lit portion and the at least one dark portion.

In some embodiments, the at least one lit portion may comprise at least one selected from the group consisting of: a tank, a trough, a pond, and a raceway pond. In some embodiments, the at least one dark portion may comprise at least one selected from the group consisting of: a foam fractionation device, a centrifuge, an electrodewatering device, a gas exchange device, and a contamination device. In some embodiments, the at least one lit portion of the bioreactor system comprises a layer of the inner volume of a bioreactor which light penetrates and the at least one dark portion of the bioreactor system comprises a layer of the inner volume of the same bioreactor in which light does not penetrate.

In some embodiments, the bioreactor system may be an open system. In some embodiments, the bioreactor system is a closed system. In some embodiments, the circulation system comprises at least one selected from the group consisting of a pump, a submersible thruster, and a paddlewheel. In some embodiments, the bioreactor system further comprises at least one inorganic carbon supply device, at least one gas supply device, a cover over at least par to the bioreactor system, and combinations thereof. The light source may comprise at least one selected from the group consisting of natural light and an artificial lighting device.

In another embodiment of the invention, a mixotrophic bioreactor system comprises: an open raceway pond comprising an inner volume of a consistent depth, the raceway pond comprising: two straight away portions separated by a center wall and bounded by straight outer walls and a floor, two U-bend portions connecting the two straight away portions to form a continuous loop, and bounded by a curved outer wall and a floor; at least one arched turning vane disposed within each U-bend portion; at least one submersible thruster disposed in the inner volume between the center wall and the outer wall of at least one of the straight away portions and suspended from above by a support structure in the inner volume a distance from the floor; and at least one organic carbon delivery device.

In some embodiments, the depth of the open raceway pond comprises 0.5 to 10 meters. In some embodiments, the open raceway pond comprises a frame structure with a liner forming a surface of the floor, center wall, and outer walls of the open raceway pond. In some embodiments, the open raceway pond comprises a molded structure with a polymer forming a surface of the floor, center wall, and outer walls of the open raceway pond. In some embodiments, the at least one submersible thruster is disposed at an end of the straight away portion within 20% of the length of the straight away portion. In some embodiments, the at least one submersible thruster is suspended a distance from the floor of 10-50% of a height of an aqueous culture volume disposed in the inner volume of the open raceway pond.

In some embodiments, the open raceway pond further comprises at least one heat exchanger. In some embodiments, the at least one heat exchanger is disposed in the at least one arched turning vane. In some embodiments, the at least one heat exchanger is disposed in the outer walls, in the center wall, in the floor, or under the floor of the open raceway pond. In some embodiments, the at least one organic carbon delivery device comprises a pH auxostat system.

In some embodiments, the open raceway pond further comprises at least one dissolved oxygen delivery device selected from the group consisting of a sparger tube, a membrane lining at least part of the floor of the raceway pond, a microbubble generator, an oxygen concentrator, a liquid oxygen injector, an oxygen saturation cone, and venturi injection by a foam fractionation device. In some embodiments, the open raceway pond further comprises a cover over at least part of the open raceway pond, at least one light source selected from the group consisting of natural light and an artificial lighting device, and combinations thereof.

In another embodiment of the invention, a turning vane comprises: a rigid structure comprising a height, width, and curvature forming an arched planar surface; and at least one functional component combined with the arched rigid structure. In some embodiments, the at least one functional component comprises an interior cavity configured to received and circulate a heat exchanger fluid. In some embodiments, the at least one functional component comprises means for delivering at least one selected from the group of organic carbon, nutrients, and gases. In some embodiments, the at least one functional component comprises an artificial lighting device. In some embodiments, the at least one functional component comprises at least one sensor. In some embodiments, the at least one functional component comprises a combination of two or more selected from the group consisting of a heat exchanger, an organic carbon delivery device, a nutrient delivery device, a gas delivery device, an artificial lighting device, and a sensor.

DETAILED DESCRIPTION

Definitions

Figure 1:
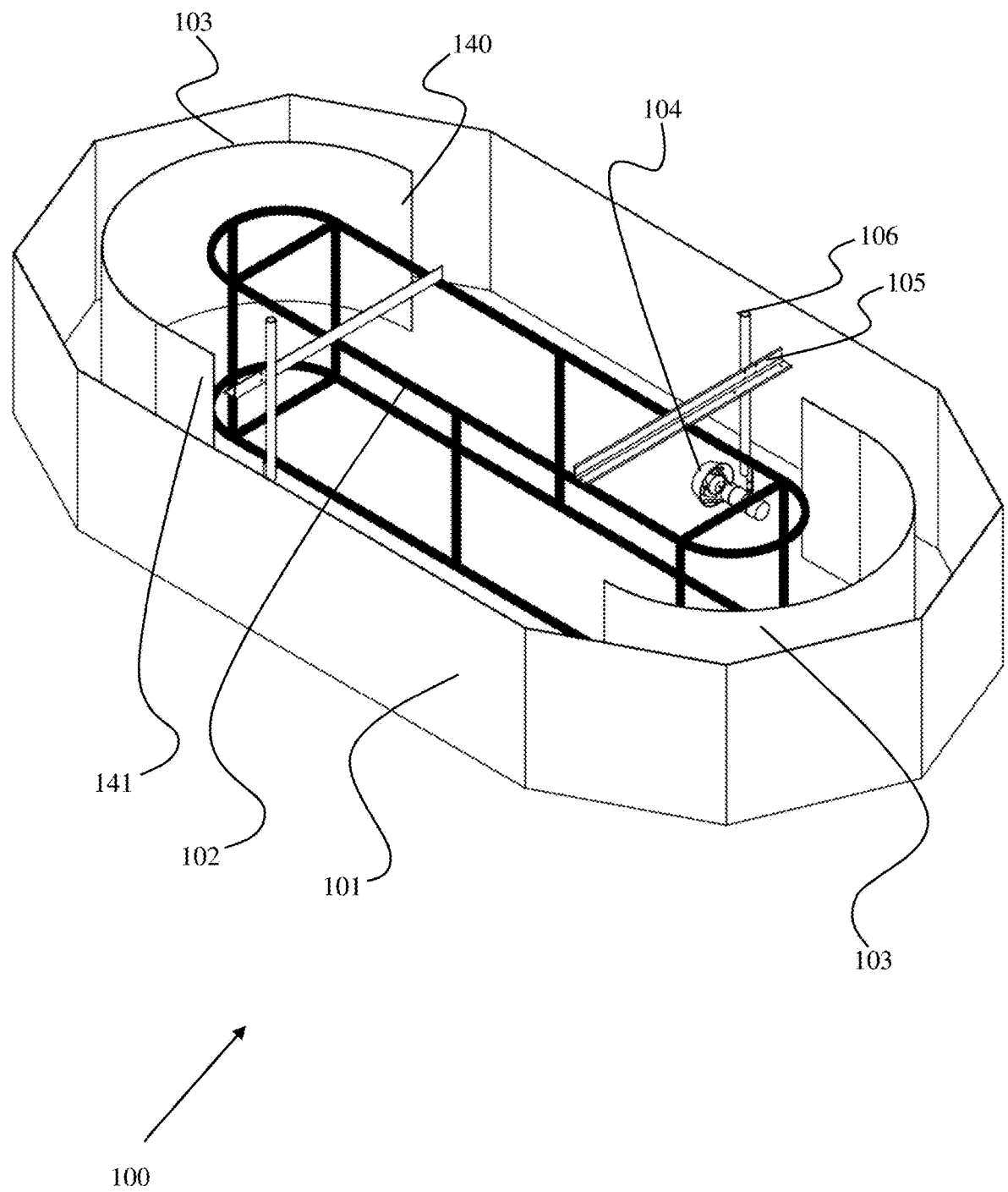
FIG. 1 shows a perspective view of an open raceway pond bioreactor embodiment with arched turning vanes and submerged thrusters.

The term "microorganism" refers to microscopic organisms such as microalgae and cyanobacteria. Microalgae include microscopic multi-cellular plants (e.g. duckweed), photosynthetic microorganisms, heterotrophic microorganisms, diatoms, dinoflagellattes, and unicellular algae.

The terms "microbiological culture", "microbial culture", or "microorganism culture" refer to a method or system for multiplying microorganisms through reproduction in a predetermined culture medium, including under controlled laboratory conditions. Microbiological cultures, microbial cultures, and microorganism cultures are used to multiply the organism, to determine the type of organism, or the abundance of the organism in the sample being tested. In liquid culture medium, the term microbiological, microbial, or microorganism culture generally refers to the entire liquid medium and the microorganisms in the liquid medium regardless of the vessel in which the culture resides. A liquid medium is often referred to as "media", "culture medium", or "culture media". The act of culturing is generally referred to as "culturing microorganisms" when emphasis is on plural microorganisms. The act of culturing is generally referred to as "culturing a microorganism" when importance is placed on a species or genus of microorganism. Microorganism culture is used synonymously with culture of microorganisms.

Microorganisms that may grow in mixotrophic culture conditions include microalgae, diatoms, and cyanobacteria. Non-limiting examples of mixotrophic microorganisms may comprise organisms of the genera: *Agmenellum, Amphora, Anabaena, Anacystis, Apistonema, Pleurochyrsis, Arthrospira* (Spirulina), *Botryococcus, Brachiomonas, Chlamydomonas, Chlorella, Chlorococcum, Cruciplacolithus, Cylindrotheca, Coenochloris, Cyanophora, Cyclotella, Dunaliella, Emiliania, Euglena, Extubocellulus, Fragilaria, Galdieria, Goniotrichium, Haematococcus, Halochlorella, Isochyrsis, Leptocylindrus, Micractinium, Melosira, Monodus, Nostoc, Nannochloris, Nannochloropsis, Navicula, Neospongiococcum, Nitzschia, Odontella, Ochromonas, Ochrosphaera, Pavlova, Picochlorum, Phaeodactylum, Pleurochyrsis, Porphyridium, Poteriochromonas, Prymnesium, Rhodomonas, Scenedesmus, Skeletonema, Spumella, Stauroneis, Stichococcus, Auxenochlorella, Cheatoceros, Neochloris, Ocromonas, Porphiridium, Synechococcus, Synechocystis, Tetraselmis, Thraustochytrids, Thalassiosira*, and species thereof.

The organic carbon sources suitable for growing a microorganism mixotrophically or heterotrophically may comprise: acetate, acetic acid, ammonium linoleate, arabinose, arginine, aspartic acid, butyric acid, cellulose, citric acid, ethanol, fructose, fatty acids, galactose, glucose, glycerol, glycine, lactic acid, lactose, maleic acid, maltose, mannose, methanol, molasses, peptone, plant based hydrolyzate, proline, propionic acid, ribose, sacchrose, partial or complete hydrolysates of starch, sucrose, tartaric, TCA-cycle organic acids, thin stillage, urea, industrial waste solutions, yeast extract, and combinations thereof. The organic carbon source may comprise any single source, combination of sources, and dilutions of single sources or combinations of sources.

The terms "mixotrophic" and "mixotrophy" refer to culture conditions in which light, organic carbon, and inorganic carbon (e.g., carbon dioxide, carbonate, bi-carbonate) may be applied to a culture of microorganisms. Microorganisms capable of growing in mixotrophic conditions have the metabolic profile of both phototrophic and heterotrophic microorganisms, and may use both light and organic carbon as energy sources, as well as both inorganic carbon and organic carbon as carbon sources. A mixotrophic microorganism may be using light, inorganic carbon, and organic carbon through the phototrophic and heterotrophic metabolisms simultaneously or may switch between the utilization of each metabolism. A microorganism in mixotrophic culture conditions may be a net oxygen or carbon dioxide producer depending on the energy source and carbon source utilized by the microorganism. Microorganisms capable of mixotrophic growth comprise microorganisms with the natural metabolism and ability to grow in mixotrophic conditions, as well as microorganisms which obtain the metabolism and ability through modification of cells by way of methods such as mutagenesis or genetic engineering.

The terms "phototrophic", "phototrophy", "photoautotrophy", "photoautotrophic", and "autotroph" refer to culture conditions in which light and inorganic carbon (e.g., carbon dioxide, carbonate, bi-carbonate) may be applied to a culture of microorganisms. Microorganisms capable of growing in phototrophic conditions may use light as an energy source and inorganic carbon (e.g., carbon dioxide) as a carbon source. A microorganism in phototrophic conditions may produce oxygen.

The terms "heterotrophic" and "heterotrophy" refer to culture conditions in which organic carbon may be applied to a culture of microorganisms in the absence of light. Microorganisms capable of growing in heterotrophic conditions may use organic carbon as both an energy source and as a carbon source. A microorganism in heterotrophic conditions may produce carbon dioxide.

The term "axenic" describes a culture of an organism that is entirely free of all other "contaminating" organisms (i.e., organisms that are detrimental to the health of the microalgae or cyanobacteria culture). Throughout the specification, axenic refers to a culture that when inoculated in an agar plate with bacterial basal medium, does not form any colonies other than the microorganism of interest. Axenic describes cultures not contaminated by or associated with any other living organisms such as but not limited to bacteria, cyanobacteria, microalgae and/or fungi. Axenic is usually used in reference to pure cultures of microorganisms that are completely free of the presence of other different organisms. An axenic culture of microalgae or cyanobacteria is completely free from other different organisms.

The term "pH auxostat" refers to the microbial cultivation technique that couples the addition of fresh medium (e.g., medium containing organic carbon such as acetic acid) to pH control. As the pH drifts from a given set point, fresh medium is added to bring the pH back to the set point. The rate of pH change is often an excellent indication of growth and meets the requirements as a growth-dependent parameter. The feed will keep the residual nutrient concentration in balance with the buffering capacity of the medium. The pH set point may be changed depending on the microorganisms present in the culture at the time. The microorganisms present may be driven by the location and season where the bioreactor is operated and how close the cultures are positioned to other contamination sources (e.g., other farms, agriculture, ocean, lake, river, waste water). The rate of medium addition is determined by the buffering capacity and the feed concentration of the limiting nutrient and not directly by the set point (pH) as in a traditional auxostat. The pH auxostat is robust but controls nutrient concentration indirectly. The pH level represents the summation of the production of different ionic species and ion release during carbon and nutrient uptake. Therefore the pH level can move either up or down as a function of growth of the microorganisms. The most common situation is pH depression caused by organic acid production and ammonium uptake. However, for microorganisms growing on protein or amino acid-rich media, the pH level will rise with growth because of the release of excess ammonia.

Overview

When culturing microorganisms in mixotrophic conditions, the application of light, inorganic carbon, and organic carbon provides multiple culture inputs, including energy sources that may be utilized by both the target microorganisms (e.g., microalgae and cyanobacteria) and contaminating organisms (e.g., fungi, bacteria, rotifers, ciliates). The presence of contaminating organisms, balance of dissolved gases, and availability of nutrients and energy sources did not have to be addressed at the laboratory scale where small volumes, short culture durations, and indoor controlled conditions were utilized.

In an outdoor large scale mixotrophic production system, the potential for contaminating organisms to inhibit the target microorganisms in the culture may influence two pathways for large scale production. The first pathway comprises an open or semi-closed system which does not operate in axenic conditions. In such non-axenic systems, the production system and culturing methods may be designed to handle the volume and diversity of contaminating microorganisms. The second pathway comprises a closed system which operates in axenic conditions. In such axenic systems, the production system may be designed to maintain the proper culture conditions in a closed system with the absence of contaminating organisms. In some embodiments, the bioreactors described may be operated in axenic conditions. In some embodiments, the bioreactors described may operate in non-axenic conditions. With the preference for some microorganism species to grow only in non-axenic conditions, the open and non-axenic embodiments described herein provide the potential for culturing a broader scope of microorganisms in mixotrophic conditions than is available for systems using axenic fermenters.

A mixotrophy bioreactor system may comprise a culturing vessel with an inner volume configured to contain an aqueous culture of mixotrophic microorganisms, at least one lighting device or a component (e.g., an opening or window with some degree of transparency) to allow the inner volume exposure to at least some light (natural, artificial, or a combination thereof), and an organic carbon supply device. In some embodiments, the mixotrophy bioreactor system may further comprise a supply of inorganic carbon (e.g., carbon dioxide, bi-carbonate). In some embodiments, the mixotrophy bioreactor systems may further comprise: an automated sensor and controls system; a programmable logic control system; at least one sensor for detecting culture parameters such as temperature, pH, dissolved oxygen, dissolved carbon dioxide, flow rate, turbidity, and photopigments or carotenoids; at least one component for mixing and circulating the culture; a gas supply (e.g., air, oxygen, nitrogen); and at least one heat exchanger. In some embodiments, the mixotrophy bioreactor system may be disposed at least partially outdoors. In some embodiments, the mixotrophy bioreactor system may be disposed at least partially indoors. In some embodiments, the mixotrophy bioreactor system may comprise a cover at least partially shielding the microorganism culture from environmental elements such as light, temperature, heat, wind, air borne particles, and precipitation. In some embodiments, the bioreactor may comprise a culturing vessel such as, but not limited to, a tank, bag, pond, raceway pond, or trough configured to allow at least some exposure to an inner volume of the culturing vessel to artificial or natural light, and an organic carbon supply device.

Dissolved Oxygen (DO) Distribution

One challenge not addressed with the laboratory scale bioreactors is the distribution of dissolved oxygen within the bioreactor volume. While a mixotrophic microorganism may produce oxygen when utilizing light as an energy source and inorganic carbon as a carbon source, oxygen is consumed when utilizing organic carbon as an energy and carbon source. Therefore, maintaining a dissolved oxygen level in the culture is important for maintaining growth rates driven by the utilization of organic carbon. In a small volume bioreactor, the dissolved oxygen content may be relatively uniform across the depth of a mixotrophic culture. Additionally, a small volume bioreactor may be easily illuminated in a substantially uniform manner, therefore allowing the metabolism of all microorganisms in the laboratory or bench top scale bioreactor to be functioning essentially in the same manner.

When the depth of the bioreactor is increased, a gradient distribution of dissolved oxygen may form over the depth of the bioreactor when mixing does not sufficiently distribute the dissolved gases in a uniform manner. The lighting in a large volume bioreactor also may not be uniform due to the depth of the bioreactor. In one non-limiting example, light may be available within a short distance (e.g., less than 10 cm) of the air/liquid interface of an open pond bioreactor and rely on mixing to periodically circulate the microorganism through the different depths of the culture volume to expose the microorganisms to intermittent light.

Below the light path distance, the available energy source would be organic carbon in a mixotrophic culture. Therefore factors that may contribute to the distribution of dissolved gases in a mixotrophic culture may comprise: 1) the mixing regime used in the bioreactor system, and the ability of the mixing regime to uniformly mix and distribute dissolved gases; 2) the loss of gases at the air/liquid interface (e.g., bursting of bubbles that do not dissolve in the aqueous medium); 3) the location of the gas supply within the bioreactor system (e.g., at the deepest portion of the bioreactor, between the air/liquid interface and the deepest portion of the bioreactor, within a turbulent flow region, within a laminar flow region); 4) the residence time of the supplied gas bubbles within the culture; 5) the consumption rate of gases by the microorganisms due to metabolic activity and available energy sources; and 6) the production of gases by the microorganisms due to metabolic activity and available energy source.

The large scale bioreactor may circulate the mixotrophic microorganisms through the volume of the bioreactor and the distribution of dissolved oxygen concentrations. The circulation through the depth of the large scale bioreactor may allow the mixotrophic microorganism to maximize the utilization of the available energy sources in the different locations for growth and product development without experiencing stress from quickly changing culture conditions.

In some embodiments, the dissolved oxygen concentration in the culture medium at the deepest portion of the bioreactor and at the air/liquid interface may vary between 10 and 500%, including a concentration at the deepest portion of 1 to 500% greater than the dissolved oxygen concentration at the air/liquid interface. The difference in dissolved oxygen concentration at the deepest portion and the air/interface may be the largest when the air or oxygen introduction device is disposed at or near the bottom of the reactor. In one non-limiting example, the depth of the bioreactor may be such that the dissolved oxygen concentration may vary between about 1 g/L and 1.1-5 g/L. In some embodiments, the depth of the bioreactor may be greater than 0.5 meters. In some embodiments the depth of the aqueous culture in the bioreactor may be between 0.5 and 10 meters, and preferably between 0.5 and 2 meters. In other embodiments, the mixing within the culture volume is sufficient to distribute the dissolved oxygen in a substantially uniform concentration across the depth of the culture volume, (e.g., within 10%).

Temperature Fluctuation

Another challenge not addressed by laboratory or bench top scale bioreactors in mixotrophic culture conditions with a small volume is the change in temperature of the culture volume. Laboratory and bench top scale bioreactors may function with a small volume (i.e., thermal mass) because they are in a controlled environment for typically a short duration of time. In a small volume bioreactor or a bioreactor with a shallow depth for light path purposes, the temperature of the culture medium may be susceptible to large changes when placed in a commercial environment, such as outdoors where the night/day cycle, weather, and clouds may change the surrounding temperature substantially over a period of hours. Changes in temperature may stress the mixotrophic microorganisms, or decrease the efficiency of growth or product formation during periods when the temperature is outside of an optimal range. When the temperature of the culture of microorganisms cannot be consistently maintained on its own, methods of cooling and heating may need to be added to the bioreactor system resulting in lower energy efficiency and high capital costs for the system.

When the depth of the bioreactor is increased to hold a larger culture volume, the larger thermal mass may be less sensitive to the temperature swings caused by heating during the daylight and cooling during the night. By design, the large scale mixotrophic bioreactor will have a culture volume with more thermal inertia than the laboratory and bench top bioreactor designs, and thus may be subject to thermal gradients, both spatially and temporally. Some embodiments of these large scale bioreactors may by physically located outdoors thus being exposed to large variations in environmental conditions. In some embodiments, the large scale bioreactor may use methods of cooling and heating to aid in the establishment of controlled growth environments and may use a control system to aid in thermal control.

In some embodiments, the bioreactor may comprise a sufficient volume and depth to reduce the average temperature change over a 24 hour period to less than a 1-20° C. difference without the use of heat exchangers, and preferably less than a 1-10° C. difference. In some embodiments, the depth of the aqueous culture in the bioreactor may be greater than 0.5 meters. In some embodiments the depth of the aqueous culture in the bioreactor may be between 0.5 and 10 meters, preferably between 0.5 and 2 meters. Therefore, a large volume culture may not need a proportionally larger use of heat exchangers as a small volume culture to maintain an optimal temperature due to the larger thermal mass of the large volume culture, and the amount of energy per volume of culture needed to control temporal changes in culture temperature may be less than small volume cultures.

In some embodiments, passive cooling, natural evaporative cooling, or evaporative cooling assisted by fan forced airflow over the surface of the microorganism culture volume may increase the thermal stability of the microorganism culture. Parameters that may affect a passive or evaporative cooling system on a bioreactor system may comprise: time of day, day of year, geographic location, position of the sun, solar heating load, humidity, moisture content, temperature, water partial pressure, Fresenl-law reflectivity of a cover, transmissivity of a cover, reflection within the bioreactor system, nocturnal re-radiation of energy between the bioreactor and sky, water evaporation, and bioreactor air flow turbulence. Heat exchangers in contact with bioreactor surfaces, culture volume, or combinations thereof may also be used to assist in the maintenance of a consistent temperature or effect spatial temperature distribution through heating or cooling.

Mixotrophic Bioreactor with Light and Dark Portions

Conventional bioreactors designed for phototrophic growth of microorganisms in an aqueous culture focus on systems with short light paths. In an aqueous microorganism culture, light may only penetrate a distance as little as 2-5 cm into the culture. By using bioreactors with short light paths, a larger percentage of microorganisms in the bioreactor system are exposed to light for energy in the photosynthesis process, and self-shading of the microorganisms may be mitigated. Short light paths may be achieved by reducing the depth of the culture or distance that light has to penetrate, essentially dictating long and shallow or narrow reactors that must cover a large amount of surface area to provide high volumes.

Conventional bioreactors designed for heterotrophic growth of microorganisms are not concerned with the availability of light and may comprise larger and deeper volumes in a smaller footprint than a comparable volume of a phototrophic reactor. In these heterotrophic systems, mechanical mixing and closing the system are important to ensure that the microorganisms are: maintained in suspension; receiving the administered dissolved oxygen and organic carbon; and preventing the introduction of competing and contaminating organisms. While mechanical mixing may be effective for distributing the organic carbon source and gas transfer, some types of mechanical mixing (e.g., open propellers, stirrers) may also impart a shear stress on the microorganisms that may potentially harm the microorganisms if the shear stress level is above the tolerance level of the microorganisms. The flexibility of mixotrophic microorganisms to utilize multiple energy sources allows a mixotrophic bioreactor system to be less constrained in design by the limiting features of light path, mixing devices, or closing of the system.

In some embodiments a mixotrophic bioreactor system for culturing microorganisms in an aqueous culture medium may comprise an organic carbon supply device, at least one lit portion receiving at least some light, and at least one dark portion receiving no light. In some embodiments, the at least one lit portion and the at least one dark portion may be components of a single apparatus, such as a deep bioreactor in which the lit portion may be layered on top of or below the dark portion. In some embodiments, the at least one lit portion and the at least one dark portion may be separate apparatuses connected in fluid communication. In some embodiments, the bioreactor system may comprise at least one portion that is open. In some embodiments, the bioreactor system may comprise at least one portion that is closed. The culture of mixotrophic microorganisms may be circulated between the at least one lit portion and at least one dark portion by any known means such as, thrusters, pumps, paddlewheels, and gravity. In some embodiments, the lit and dark portions may be the physical components of the bioreactor system, with the lighted and dark nature controlled by the timing and use of artificial light devices.

In an alternate embodiment, the method of mixing may enable a vertical flow pattern such that the fluid may be swept from top to bottom in a rotating fashion to bring the cells to the light at a faster frequency. In one non-limiting example, the use of a submerged thruster creates a rotation, vertical, or swirling flow that brings the microalgae or cyanobacteria cells to the air/liquid interface of the aqueous culture to provide exposure to light (i.e., lit portion) several times before returning to a depth of the aqueous culture comprising a dark portion. One advantage of providing additional light in a mixotrophic culture of microalgae or cyanobacteria is the reduction of carbon energy to drive growth, formation of pigments, formation of proteins, formation other products that are preferentially formed in the presence of light, and combinations thereof.

In some embodiments, the circulation between the at least one lit portion and the at least one dark portion create a light duty cycle for mixotrophic microorganisms of 2 to 25%, and preferably 5%. The light duty cycle is defined as the fraction of a total light-dark microcycle in which an individual microorganism is exposed to light. The light duty cycle is calculated by dividing the time the microorganisms are exposed to light by the total time the microorganisms spend in the bioreactor system. The calculated light duty cycle is expressed as a percentage. In some embodiments, the bioreactor may comprise a plurality of strategically spaced lit and dark portions to create a repeating light duty cycle when the culture of microorganisms is circulated, which may be controlled by the flow rate of the culture of microorganisms. In some embodiments, the light duty cycle may also be controlled by the timing and use of artificial lighting devices.

The at least one lit portion exposes the culture of mixotrophic microorganisms to at least some light from a light source. In some embodiments, the light source may comprise at least one lighting device providing artificial light. The at least one artificial lighting device may comprise any lighting device capable of providing light to a culture of microorganisms such as, but not limited to, fluorescent tubes, light emitting diodes (LED), micro LEDs, high pressure sodium lamps, high intensity discharge lamps, neon lamps, metal vapor lamps, halogen lamps, sulfur plasma lamps, and incandescent bulbs. In some embodiments, the at least one lighting device may be selected or tuned to provide light of a particular wavelength spectrum or combination of spectrums such as, but not limited to, violet (about 380-450 nm), blue (about 450-495 nm), green (about 495-570 nm), yellow (about 570-590 nm), orange (about 590-620 nm), red (about 620-750 nm), and far red (about 700-800 nm), infrared (IR) (about 1,000-20,000 nm) and ultraviolet (UV) (about 10-400 nm). In some embodiments, the application of light may be continuous, discontinuous, flashing, or pulsing to create any desired light/dark cycle. In some embodiments, the intensity of light supplied by the at least one lighting device may comprise a constant intensity or variable intensity. The at least one lighting device may be mounted anywhere on the bioreactor module, suspended or submerged in the culture volume, or may be separate from the bioreactor module.

In some embodiments, the light source may comprise natural light such as sunlight. In some embodiments, the lit portion receiving sunlight may comprise a cover configured to block at a least a portion of the sunlight from contacting the culture of microorganisms. In some embodiments, the cover may block between 5-95% of light. The cover may comprise a semitransparent photovoltaic panel, a film which selectively blocks light in a specific wavelength range, a passive shade cloth (e.g., an aluminet shade cloth, a shade cloth that blocks some light or blocks specific wavelengths), a semitransparent polymer, tinted glass, and combinations thereof. In some embodiments, the lit portion may be a portion of a large volume and deep pond, trough, or tank in which light penetrates such as, but not limited to, the air/water surface interface and top fraction of a deep pond or tank experiencing light penetration. The at least one lit portion may receive light at 100-2,500 µmol photons/$m^2$ s, preferably 200-500 µmol photons/$m^2$ s. In some embodiments, the light source may comprise a combination of at least one lighting device providing artificial light and natural light (e.g., sunlight).

The at least one dark portion comprises the absence of light for the culture of mixotrophic microorganisms. In some embodiments, the at least one dark portion may comprise a cover of opaque material configured to prevent light from contacting the culture of microorganisms. In some embodiments, the at least one dark portion may comprise the depth of a large volume below where light may penetrate. In some embodiments, the at least one dark portion may comprise a functional apparatus in fluid communication with the at least one lit portion. The functional apparatus may comprise a foam fractionation device (e.g., protein skimmer, bubble column, dissolved air flotation tank), centrifuge, electrode-watering device (e.g., reactor exposing the culture to an electric field), dewatering device (e.g., filtration apparatus, sedimentation tank), contamination control device (e.g., device for applying ozone or other contamination control solutions), gas exchange device (e.g., degassing tank), holding tank, and combinations thereof.

In one non-limiting example, the at least one dark portion comprises a protein skimmer with adjustable settings which provides a plurality of functions while shielding the culture of microorganisms from light, such as: gas injection; degassing; and removal of foam and constituents such as contaminating microorganisms, suspended solids, debris, and clumped microorganisms above a threshold size from the culture through foam fractionation. The removal of foam and constituents from the culture may reduce competition for resources with the mixotrophic microorganisms and extend the life of the culture of mixotrophic microorganisms.

Bioreactor System Embodiments

The following bioreactor system embodiments incorporate the described differences between conventional phototrophic or heterotrophic systems and mixotrophic systems, and small volume and large volume mixotrophic cultures regarding dissolved oxygen distribution, temperature fluctuation, and access to light for successful mixotrophic culturing at a large scale in a bioreactor system with lit and dark portions. In a first non-limiting embodiment, a large scale mixotrophic bioreactor system configured for culturing microorganisms in an aqueous culture medium may comprise a raceway pond, trough, or tank bioreactor providing a lit bioreactor configured for containing an aqueous culture in an inner volume that receives at least some light from a light source, and a foam fractionation apparatus (e.g., protein skimmer, bubble column) providing the dark portion of the bioreactor system with an opaque tank section configured for containing an aqueous culture in an inner volume that receives no light. The lit bioreactor may be in fluid communication with the foam fractionation apparatus through conduits attached to an inlet and outlet of the lit bioreactor to circulate the aqueous culture medium between lit and dark portions. The depth of the lit bioreactor may be designed for a culture volume size with a sufficient thermal mass to aid in the control of temperature fluctuations The culture of microorganisms may be circulated by pumps, paddlewheels, or thrusters in the lit bioreactor, and upon exiting the lit bioreactor through an outlet the culture flows to the foam fractionation apparatus. In some embodiments, gas injection (e.g., oxygen, air, carbon dioxide, nitrogen) for dissolved gas manipulation may be performed by the foam fractionation apparatus by venturi injection, sparger, air muffler, microbubble generator, and the like. Upon exiting the foam fractionation apparatus, the culture returns to the lit bioreactor. Using the gas injection of the foam fractionation apparatus may aid in controlling the dissolved oxygen concentration by allowing the gas to be injected at a single point where the residence time can be controlled by the flow rate through the circulation back to the lit bioreactor where the aqueous media may be thoroughly mixed. In some embodiments, organic carbon may be dosed by a metering pump into the discharge line of the foam fractionation apparatus, which returns the culture to the lit bioreactor and completes the culture circulation path within the bioreactor system. In some embodiments, the organic carbon may be dosed directly into the lit bioreactor, or dosed directly within the foam fractionation apparatus. In some embodiments, the organic carbon may comprise acetic acid and may be dosed using a pH auxostat system.

In some embodiments, the culture parameters (e.g., pH, temperature, dissolved oxygen, dissolved carbon dioxide)

may be detected by probes and sensors at various locations along the circulation path such as, but not limited to: within the foam fractionation device, at the inlet of the foam fractionation device, at the outlet of the foam fraction device, and within the lit bioreactor. In some embodiments, the lit bioreactor may be at least partially covered with a cover that blocks at least some light. In some embodiments, the cover may comprise a canopy or a greenhouse. In some embodiments, the cover may comprise a low profile cover. In some embodiments, the cover may comprise a material that blocks transmission of between 1% and 99% of light to the culture, such as but not limited to a passive shade cloth. In some embodiments, the cover may comprise a film which selectively blocks transmission of certain wavelengths of light to the culture, or semitransparent photovoltaic panels.

In some embodiments, at least one fan may be disposed in the cover of the system to facilitate forced air circulation across the surface of aqueous culture and the head space between the cover and the surface of the aqueous culture. In some embodiments, the circulation of the aqueous culture through the bioreactor system may be adjusted to a desired duty cycle comprising the amount of time the culture spends in the foam fractionation apparatus compared to the total time in the bioreactor system.

In some embodiments, gases may be supplied to the culture through aeration tubing disposed within the lit bioreactor in addition to the gasses supplied by the foam fractionation apparatus. In some embodiments, a heat exchanger (e.g., coils fed with heat exchanger fluid) may be submerged in the culture volume of the lit bioreactor or in the opaque tank section of the foam fractionation apparatus. The foam fractionation apparatus may also provide the function of removing foam from the aqueous culture, as foam has been known to harbor contamination and thus removal of the foam helps to maintain the health of the microorganism culture.

In a further embodiment of the lit bioreactor, the bioreactor may comprise an open raceway pond with two straight away portions separated by a center wall, two U-bend portions connecting the straight away portions into a closed loop, at least one organic carbon delivery device, and at least one submersible thruster to provide the mixing and circulation of the aqueous culture through the closed loop. The straight away portions and U-bend portions of the open raceway pond form a continuous looped fluid circulation path for the aqueous culture defined by outer wall surfaces of the U-bend and straight away portions and the outer surfaces of the center wall. Along this continuous looped fluid circulation path, the culture is provided with at least some light, nutrients, and organic carbon. The open raceway pond may receive light from a natural light source (e.g., sunlight), an artificial light source, or combinations thereof. The open raceway pond may be constructed above ground with a frame or molded body, or may be constructed in the ground.

In some embodiments, the width of the open raceway pond may comprise about 3 to 12 meters (about 10 to 40 feet) total and preferably about 9 meters (about 30 feet), with the length dependent on the desired culture volume. In some embodiments, the height of the bioreactor may be 1 to 12 meters to allow for a culture depth of 0.1 to 10 meters, preferably between 0.5 and 2 meters. In some embodiments, the culture may be started at a first depth and then increase to a maximum culture depth as the culture density increases after inoculation. The depth of the open raceway pond bioreactor incorporates the concepts previously described of a dark portion layered with lit portions in the same culture volume (e.g., a dark portion below the distance light penetrates the top culture surface, a dark portion beyond the distance light from submerged lighting devices reaches within the culture volume), and the thermal stability of a larger culture volume to reduce or eliminate the requirements for heat exchangers.

In some embodiments, the center wall separating the straight away portions may be about 0.1-0.6 meters (about 6-24 inches) in width, preferably about 0.25 meters (about 10 inches), and of a height which protrudes above the depth of the aqueous culture. The floor of the open raceway pond may be flat, contoured, or combinations thereof. In some embodiments, the contoured floor of the raceway pond is V or U shaped. In some embodiments, the floor may be flat to create an inner volume of the open raceway pond with a consistent depth along the looped culture flow path.

A series of different sized open raceway pond bioreactors may be used together in a system for culturing mixotrophic microalgae, with the volume of the ponds increasing to accommodate the increase of culture density at different stages. A first pond bioreactor may comprise a culture volume of 15,000 to 20,000 liters. A second pond bioreactor may comprise a culture volume of 100,000 to 130,000 liters. A third pond bioreactor may comprise a culturing volume of over 500,000 liters. The depth may be the same for each pond bioreactor, regardless of the volume, but the width and length may change for the different volumes. For example, a 100,000 liter pond bioreactor may comprise a width of about 4.5 meters (about 15 feet) and a length of about 27 meters (about 89 feet) comprising a width to length ratio of about 1:6; and a 500,000 liter pond bioreactor may comprise a width of about 9 meters (about 30 feet) and a length greater than 27 meters (about 90 feet).

In some embodiments, the open raceway pond may be molded from a polymer as one piece or in sections that are coupled together. In some embodiments, the raceway pond may comprise a rigid frame covered with a liner material. The liner material may be selected to resist degradation caused by low pH culture solutions, the organic carbon, and other constituents of the microorganism culture. Examples of suitable liners include Lake Tahoe liner, F-Clean NEW soft-shine white (100 μm), Raven (821 W Algonquin St, Sioux Falls, S.Dak. 57104) 20 mil grey/black, Raven 20 mil white/white, and Western Environmental Liner (8121 W. Harrison, Tolleson, Ariz. 85353) polypropylene liner (45 mil). The rigid frame may comprise wood, plastic, metal, and similar suitable materials.

In some embodiments, the bioreactor system may comprise at least one arched turning vane in each of the U-bend portions, and may comprise two or more turning vanes in each of the U-bend portions dependent on the volume and size of the bioreactor. The turning vanes comprise a height, width, and curvature forming an arched planar surface for guiding the flow of the aqueous microorganism culture. The turning vanes are designed to facilitate the flow of the aqueous culture through the U-bend portions, and change the direction of the flow to follow the 180 degree turns into the straight away portion upon exiting the U-bend portion. In some embodiments, the downstream end of the turning vane may comprise an asymmetrical curved design extending past the beginning position of the upstream portion of the turning vane and into the beginning of the straight away portion. In some embodiments, the turning vanes comprise a symmetrical curved design. In some embodiments, the upstream end of the turning vane may begin wherein the straight away portion ends and the U-bend portion begins. In some embodiments, the turning vanes may also create a passive vortex through the end-wall boundary layer migration that aids in mixing the aqueous culture during circulation. In some embodiments, the turning vanes disposed in the same or different U-bend portions may have the same curvature profile. In some embodiments, the turning vanes disposed in the same or different U-bend portions may have different curvature profiles, including groups of the turning vanes in the same U-bend portion with different curvature profiles.

The height of the turning vanes may be greater than the depth of the aqueous culture. In some embodiments, the turning vanes may be secured to the floor of the open raceway pond and at the top to the center wall and outer walls of the U-bend portion by support members, and secured at the base to the floor of the U-bend portion. The turning vanes and support members may comprise suitable polymers or metals (e.g., stainless steel) suitable for microorganism culturing formed by smooth solid material, or rigid frames with a surface comprising liner material, polymer sheets, or sheets of metal mounted to the frames.

One design emphasis for the open raceway pond bioreactor is the minimization of the equipment disposed within the culture volume that may provide a surface for contamination to accumulate and proliferate. With the turning vanes already disposed in the culture volume, at least one other functional component may be added to, combined with, or integrated with the rigid structure of the turning vanes to provide functionality beyond guidance of fluid flow and minimize the number of separate components disposed in the culture volume. In some embodiments, the rigid structure of the turning vanes may comprise an arched rigid structure frame with a material forming the surface such as, but not limited to, a liner material, polymer, or sheet metal. The material covering the frame provides sufficient spacing within the frame to house at least one functional component. The rigid frame may comprise wood, metal, plastic, or similar suitable materials. In some embodiments, the at least one functional component may form the surface of the turning vane.

In some embodiments, the at least one other functional component may comprise a heat exchanger, such as but not limited to tubular or plate heat exchangers configured to receive and circulate heat exchanger fluid. In some embodiments, the at least one other functional component may comprise a device such as, but not limited to conduit, nozzles, injectors, bubblers, and pumps for delivering a nutrient medium, organic carbon, or other nutrients. In some embodiments, the at least one other functional component may comprise a device such as, but not limited to conduit, nozzles, injectors, bubblers, and pumps for delivering gases (e.g., oxygen, carbon dioxide, air). In some embodiments, the at least one other functional component may comprise an artificial lighting device such as, but not limited to LEDs. In some embodiments, the at least one other functional component may comprise sensors or probes.

In some embodiments, the turning vanes may comprise an arched rigid structure that does not include a separate frame, such as a single piece, two piece, formed, or molded structure. In some embodiments, the at least one other functional component may be integrated with the frameless rigid structure of the turning vane. Integrating the at least one other functional component into the rigid structure may reduce the thickness of the turning vane compared to a turning vane comprising a frame. In one non-limiting embodiment, the turning vane may comprise an arched structure comprising a cavity, such as sheets of material (e.g., metal, plastic) joined at the edges to form an interior cavity that may circulate or serve as a conduit for a fluid (e.g., heating fluid, gas, organic carbon solution, nutrient solution). The surfaces of the sheets of material may be smooth or contoured.

In some embodiments, the integrated structure of the turning vane may only contain openings for allowing a fluid to be introduced into the interior cavity from a reservoir, circulated with the cavity, and returned to the reservoir, such as for heat exchanger fluid that provides a function by circulation within the cavity for heat transfer with a the culture without introduction into the culture volume. The cavity may comprise additional internal partitions to guide exchange fluid through a flow path or distribute the fluid evenly throughout the cavity. In some embodiments, the integrated structure of the turning vane may comprise additional openings allowing the fluid to exit the interior cavity for introduction into the culture volume, such as when the interior cavity serves as a conduit for introducing a gas, organic carbon, or nutrients into the culture volume. In some embodiments, the multi-functional turning vane may comprise a combination of functions beyond the guidance of fluid flow such as a combination of two or more functions selected from the group consisting of a heat exchange, organic carbon delivery, nutrient delivery, gas delivery, artificial lighting, and parameter sensing.

In some embodiments, the bioreactor system may comprise plate or tubular heat exchangers disposed in the raceway pond underneath the liner, in the outer walls, in the center wall, in the floor, under the floor, and combinations thereof. In some embodiments, the heat exchangers may comprise a combination of heat exchangers disposed within the turning vanes and in the raceway pond underneath the liner, in the outer walls, in the center wall, in the floor, or under the floor. By positioning the heat exchanger within the turning vane or underneath the liner, the number of components submerged in the aqueous culture on which contamination may grow on or adhere to may be minimized, thus providing a healthier environment for the culture of microorganisms. Depending on the location of the heat exchangers, a plate heat exchanger disposed within or under a raceway pond bioreactor surface may provide more surface area for heat exchange than a tubular heat exchanger. A heat exchange fluid for circulation in the heat exchangers to cool or heat the aqueous culture may be provided by conduits between the heat exchangers and a fluid reservoir. In other embodiments, the bioreactor may comprise a heat exchanger (e.g., a tube and shell heat exchanger) disposed outside of the bioreactor volume through which a volume of the aqueous culture is circulated through for heat exchange.

Submersible thrusters are commercially available from a number of sources, such as Xylem (1 International Drive, Rye Brook, N.Y., 10573) which produces the Flygt brand of submersible jet ring thrust mixer products. The number of submersible thrusters may be dictated by the volume of the aqueous culture and length of the straight away sections of the open raceway pond, and may comprise at least 1, at least 2, at least 4, at least 8, or more to sufficiently mix the culture volume. For example an open raceway pond bioreactor with a 20,000 liter volume may use two submerged thrusters in total, consisting of a single thruster disposed at two different locations; and an open raceway pond bioreactor with a 500,000 liter volume may use at least four submerged thrusters in total, consisting of at least two thrusters disposed at least two different locations.

In some embodiments, the submersible thrusters may be disposed downstream of the turning vane in the U-bend portion of the raceway ponds in positions such as, but not limited to, at the U-bend exits and mid channel in the straight away portions. In some embodiments, the at least one submersible thruster may be disposed at an end of a straight away portion near the U-bend portion within 20% of the length of the straight away portion at the end. For example if the straight away portion is 100 meters long, the at least one submersible thruster may be disposed within the 20 meters of an end of the straight away portion (i.e., distance between the end of the straight away portion and the submersible thrusters is 20 meters or less).

In some embodiments, the at least one submersible thruster may be disposed equidistant from the center wall and the outer wall of the straight away portion. In some embodiments, the at least one submersible thruster may be disposed in the straight away portion equidistance between the two U-bend portions. In some embodiments, multiple submersible thrusters at a single location in the bioreactor may be in parallel at the same axial position, offset from each other, or staggered depending on the desired fluid movement. In some embodiments a plurality of submersible thrusters may be disposed on opposite side or ends of the bioreactor, or at intervals along the length of the bioreactor By positioning the submersible thrusters at the U-bend exit the thrust produced may be maximized in the straight line flow of the culture through the straight away portions and momentum may be added to the culture flow exiting the U-bend portions where some velocity of the culture flow may be lost due change in flow direction. In some embodiments, the at least one submersible thruster may be suspended in the inner volume of the open raceway pond a distance from the floor of the open raceway pond from above by a support structure. In some embodiments, the thrusters may be disposed at a distance measured from the floor of the raceway pond that is 10-50% of the culture volume height, preferably at a position measured from the floor of the raceway pond about 20-30% of the height of the aqueous culture volume. For example, if the culture volume height is 2 meters, the submersible thruster may be positioned between 0.2-1 meters above the floor. The depth positioning of the thrusters in the raceway pond also facilitates mixing the culture so that the microorganisms at the bottom of the culture pond depth are circulated to the air/liquid interface periodically.

The support structure suspending the submersible thrusters from above may comprise support members coupled to the center wall and outer walls of the bioreactor. In some embodiments, the support structure may comprise multiple support members coupled together in a manner (e.g., sliding and locking, discrete locking positions, friction fits, clamping) to allow the position of the submersible thruster to be adjusted vertically (i.e., in the depth of the culture volume) and horizontally (i.e., between the outer and center walls). By utilizing thrusters that may be suspended from a support structure above the culture volume, the thruster provides an advantage over a submerged traditional propeller mixer that is fixed in place with the motor located outside the raceway pond. A traditional propeller mixer is fastened to a rotating shaft which is driven by a motor, and in a raceway pond the shaft needs to be parallel to the flow direction, which would require the shaft to be submerged by penetrating one of the walls to connect to the motor disposed outside the pond. Penetration of the pond wall provides an opportunity for a leak and also limits the adjustment of the propeller positioning. A completely submersible thruster that is suspended from above may be adjusted vertically and horizontally more easily for optimal placement in culture volume for mixing than a propeller fixed in position through a pond wall. Additionally, the suspended submersible thruster does not introduce additional opportunities for a leak in the open raceway pond outer wall.

The submersible thrusters may be sized based on the culture volume size and size of the raceway pond bioreactor to sufficiently mix the culture over the entire depth of the raceway pond bioreactor and propel the culture. For example, in a 20,000 liter pond bioreactor the thrusters may be sized to produce 25 pounds of thrust. In cultures of shear sensitive microalgae or cyanobacteria, the submersible thruster may be replaced with a different mixing device, such as a paddlewheel.

An organic carbon source may be dosed within the bioreactor at multiple points by at least one organic carbon delivery device. In some embodiments, the organic carbon may be dosed at a location upstream of the mixing device (e.g., thruster, paddlewheel, pump) to allow the organic carbon to be sufficiently mixed in the aqueous culture.

In some embodiments, the dosed organic carbon may be acetic acid. In further embodiments, the dosing of acetic acid may be conducted with a pH auxostat system to both control pH and maintain grow rates of the microorganism. For example, the acetic acid flow rate may comprise 6.3 L/min of 20% acetic acid in order to achieve a growth rate of 6 g/L-day with a culture of *Chlorella*. In some embodiments, the dosed organic carbon source may be glucose, glycerol, or any other suitable organic carbon source depending on the microorganism. In some embodiments, the at least one organic carbon delivery device may comprise an outlet disposed within the open raceway pond configured to deliver organic carbon to the aqueous culture. In some embodiments, the at least one organic carbon delivery device may comprise an outlet disposed above the open raceway pond configured to deliver organic carbon to the aqueous culture. In some embodiments, the organic carbon may be delivered through a multi-functional turning vane.

In some embodiments, gases such as air, oxygen, carbon dioxide, and nitrogen, may be supplied to the culture in the bioreactor system through devices to ensure maintenance of the desired dissolved gas level such as: sparger tubes located at the bottom of the bioreactor, sparger tubes located at the base of the inner diameter and outer diameter of the raceway pond, a membrane (e.g., Prototype Tyvek) lining the bottom of at least part of the raceway pond, a microbubble generator, an oxygen concentrator, liquid oxygen injection, an oxygen saturation cone, a multi-functional turning vane, and combinations thereof. In some embodiments, a foam fractionation device, such as a protein skimmer with venturi injection may be in fluid communication with the bioreactor pond, and process the aqueous culture during circulation and introduce air or oxygen into the culture medium through venturi injection. In some embodiments, the oxygen supply devices may be sized to maintain the dissolved oxygen content above 3 mg/L in the aqueous culture of microorganisms.

In some embodiments, the open raceway pond bioreactor may be at least partially covered with a cover that blocks at least some light. In some embodiments, the cover may comprise a canopy or a greenhouse. In some embodiments, the cover may comprise a low profile cover. In some embodiments, the cover may comprise a material that blocks transmission of between 1% and 99% of light to the culture, such as but not limited to a passive shade cloth. In some embodiments, the cover may comprise a film which selectively blocks transmission of certain wavelengths of light to the culture. In some embodiments, the cover may comprise semitransparent photovoltaic panels.

In some embodiments, the bioreactor system may comprise probes or sensors to measure and monitor at least one of pH, temperature, NO₃, dissolved oxygen, dissolved carbon dioxide, turbidity, culture concentration, flow velocity, flow rate, light, and photopigments or carotenoids. The probes or sensors maybe located at one or multiple locations within the bioreactor system and disposed in mid-depth in the culture volume. In some embodiments, the pH sensors are used to control pH by organic carbon addition at locations directly upstream of the submersible thrusters. NO₃ may be added as needed manually or with automated equipment based on the values measured by the probes or sensors.

Figure 2:
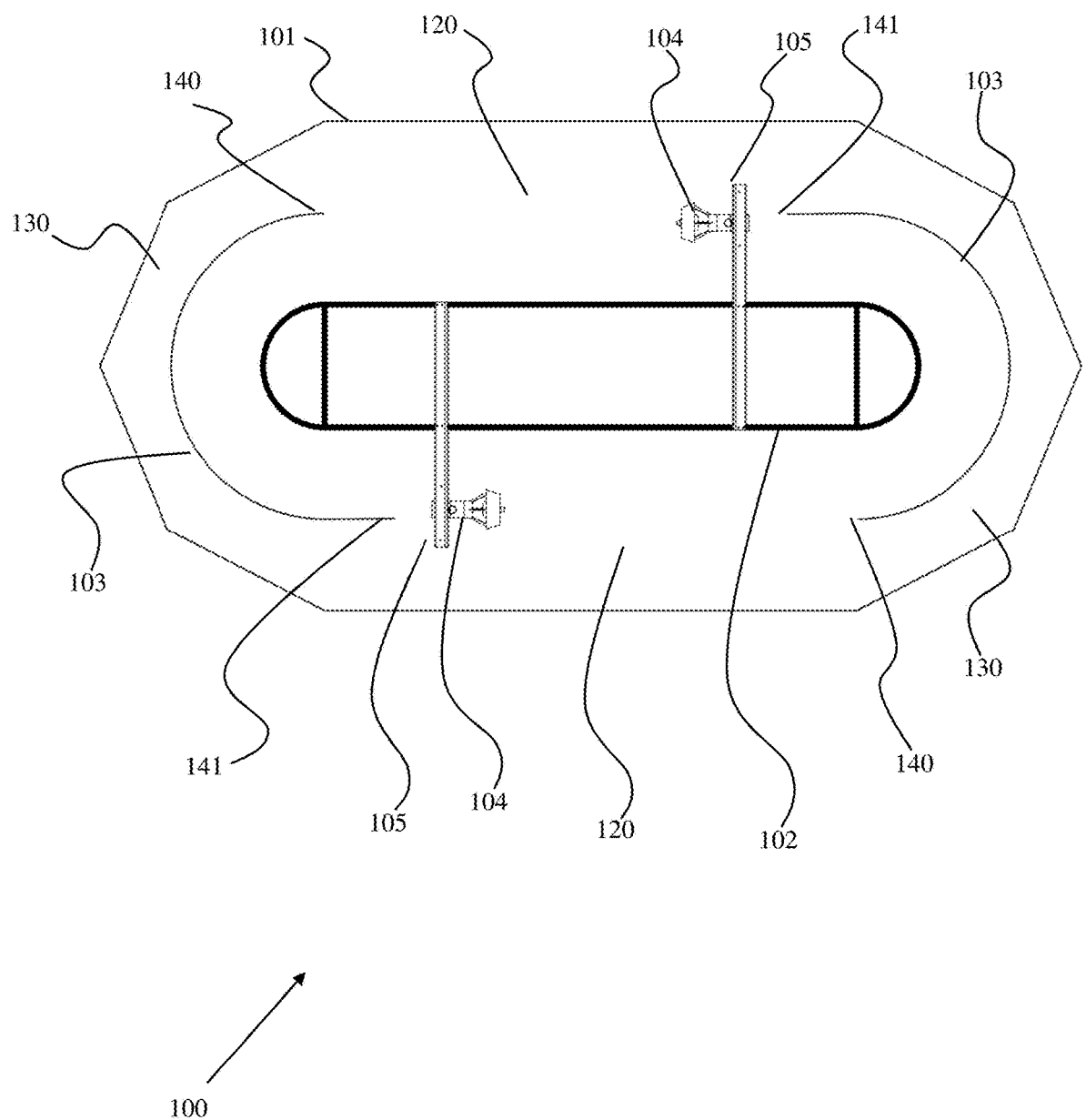
FIG. 2 shows a top view of an open raceway pond bioreactor embodiment with arched turning vanes and submerged thrusters.
Figure 3:
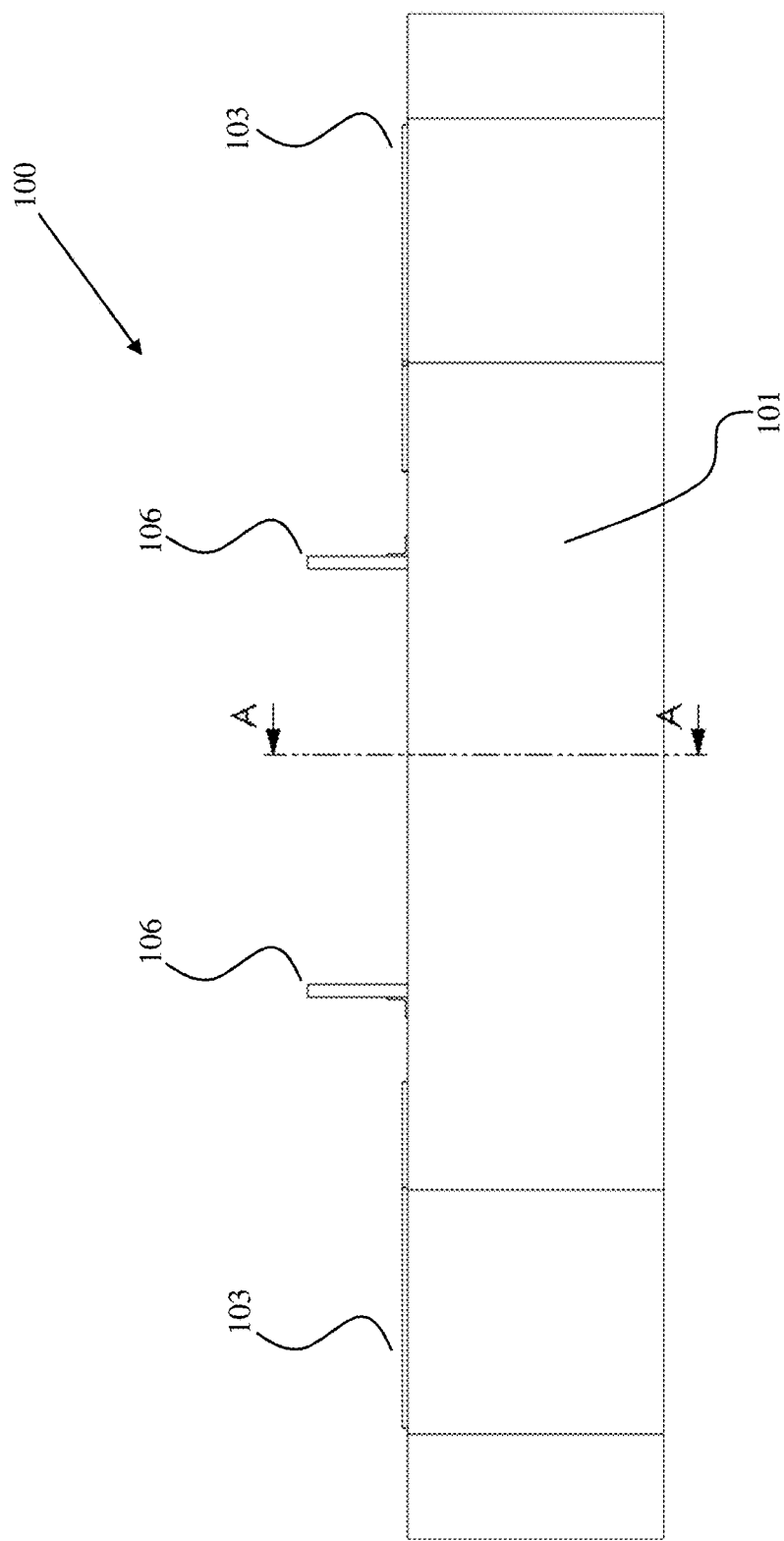
FIG. 3 shows a side view of an open raceway pond bioreactor embodiment and identifies the location of cross section A.
Figure 4:
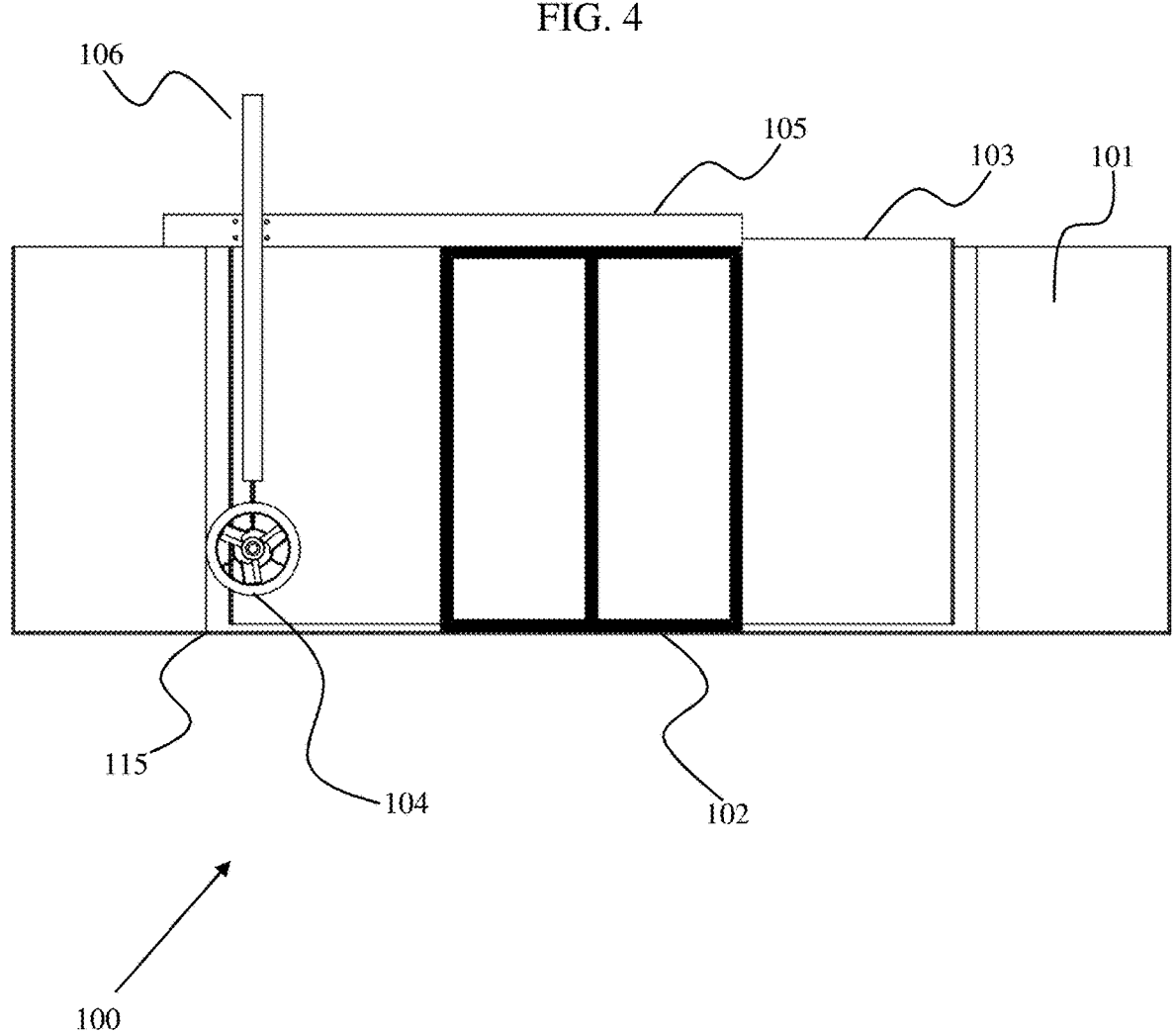
FIG. 4 shows a front view of an open raceway pond bioreactor embodiment at cross section A.
Figure 7:
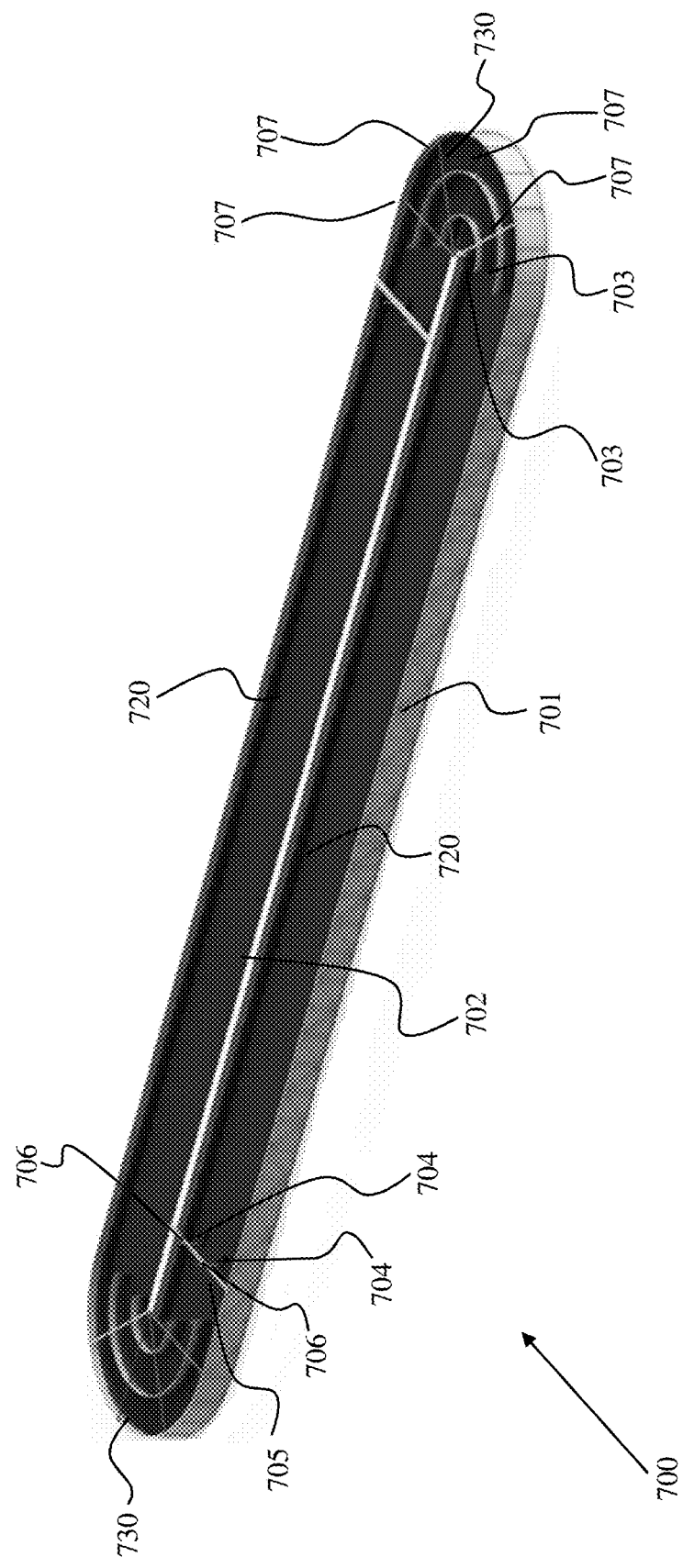
FIG. 7 shows a perspective view of an open raceway pond bioreactor embodiment with multiple arched turning vanes and submerged thrusters.

One non-limiting embodiment of the open raceway pond bioreactor is shown in FIGS. 1-4. The open raceway pond bioreactor 100 comprises an outer wall 101, center wall 102, arched turning vanes 103, submerged thrusters 104, and support structure 105 (horizontal), 106 (vertical) or the submerged thrusters. The outer wall 101 and the center wall 102 form the boundaries of the straight away portions 120 and U-bend portions 130 of the bioreactor in FIGS. 1-4. In FIGS. 1-4 the center wall 102 is shown as a frame for viewing purposes, but in practice panels are inserted into open sections of the frame or a liner placed over the frame to form a solid center wall surface. Also, the outer wall 101 of the bioreactor is FIGS. 1-4 is depicted as multiple straight segments connected at angles to form the curved portion of the U-bend 130, but the outer wall 101 may also form a continuous curve or arc as shown in FIG. 7. FIG. 4 shows a cut away view of the bioreactor 100 at cross section A as identified in FIG. 3, which further displays the submerged thruster 104 being disposed in the inner volume of the bioreactor a distance above the floor 115 of the bioreactor and spaced from the outer wall 101 and the center wall 102.

FIG. 2 further shows the asymmetrical shape of the arched turning vanes 103, first end 140 of the turning vane at the beginning of the U-bend portion 130 and the second end 141 extending past the U-bend portion into the straight away portion 120. The flow path of the culture in the open raceway pond bioreactor 100 of FIG. 2 would be counter clockwise, with the culture encountering first end 140 of the turning vane first, second end 141 of the turning vane second, and then the submerged thruster 104 when traveling through the U-bend portion 130 and into the straight away portion 120. The arched turning vanes 103 are also shown in FIGS. 1 and 3 to be at least as tall as the center wall 102, to allow a portion of the arched turning vanes 103 to protrude from the culture volume when operating.

Figure 5:
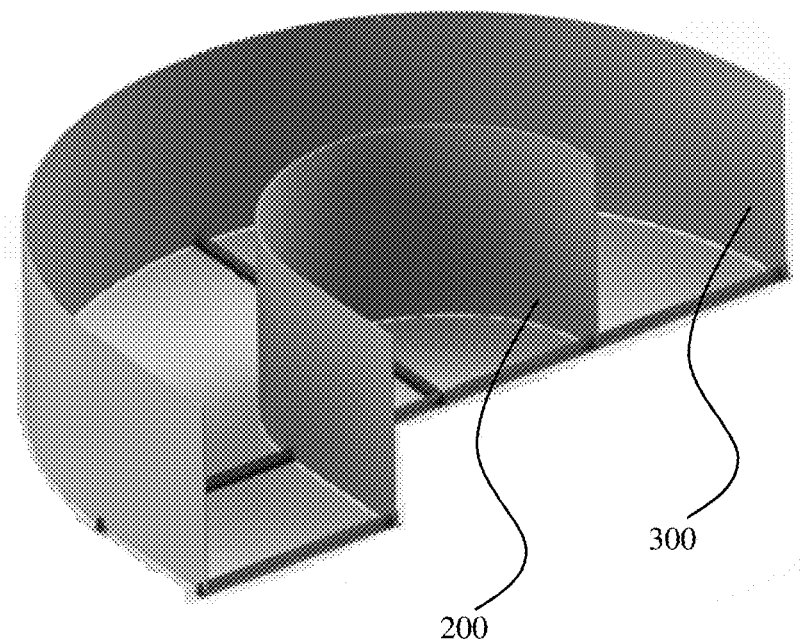
FIG. 5 shows a pair of arched turning vanes.

An embodiment of a pair of arched turning vanes for use in the U-bend portions of an open race pond bioreactor is shown in FIG. 5 with an inner turning vane 200 and an outer turning vane 300. Both turning vanes shown in FIG. 5 are asymmetrical, but the turning vanes may also be symmetrical or a combination of symmetrical and asymmetrical. The turning vanes may also have the same curvature radius or different curvature radii.

Figure 6:
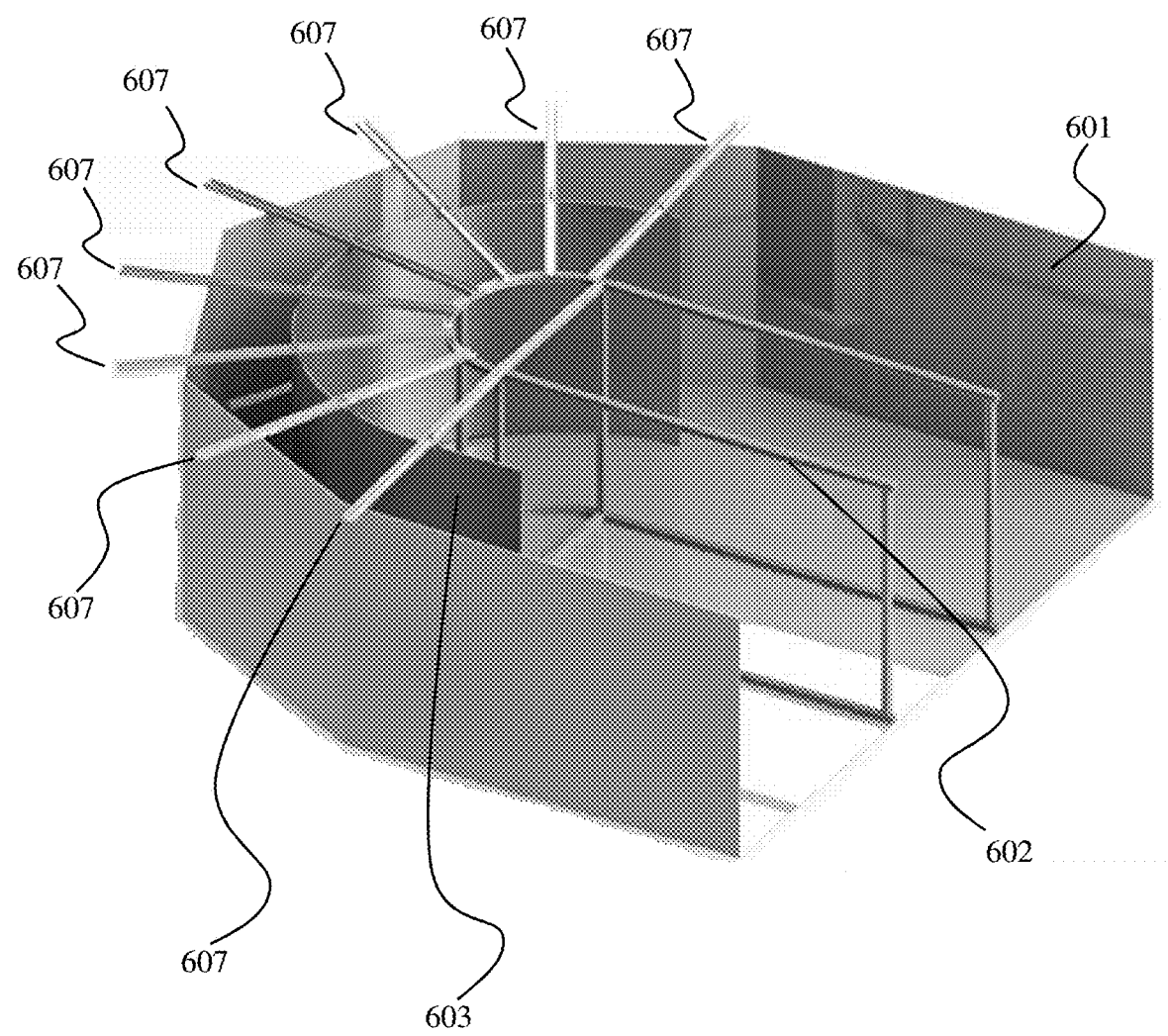
FIG. 6 shows a support structure for an arched turning vane.

An embodiment for structurally supporting an arched turning vane is shown in the view of FIG. 6. The arched turning vane 603 is supported by a plurality of structural support members 607 fastened to the outer wall 601 and the center wall 602 to stabilize the arched turning vane 603 and maintain the boundaries of the flow path through the U-bend portion defined by the outer wall 601, arched turning vane 603, and center wall 602.

An embodiment of a large volume above ground open raceway pond bioreactor with multiple turning vanes and multiple submerged thrusters is shown in FIG. 7. The open raceway pond bioreactor 700 comprises an outer wall 701, center wall 702, arched turning vanes 703, support structure 707 for the arched turning vanes, submerged thrusters 704, and support structure 705 (horizontal), 706 (vertical) for the submerged thrusters 704. The outer wall 701 and the center wall 702 form the straight away portions 720 and U-bend portions 730 of the bioreactor. The configuration of arched turning vanes 703, support structure 707 for the arched turning vanes, submerged thrusters 704, and support structure 705 (horizontal), 706 (vertical) for the submerged thrusters 704 is the same for both ends of the bioreactor 700.

Figure 8:
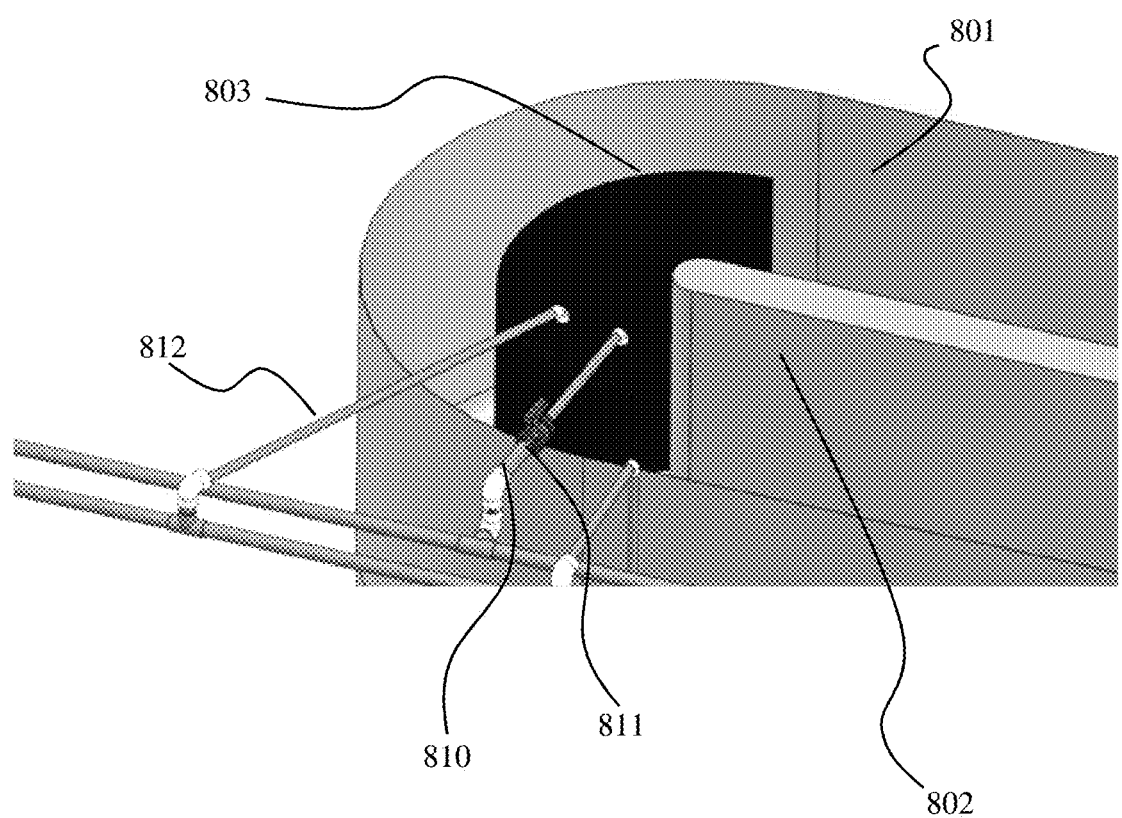
FIG. 8 shows an embodiment of a multi-functional turning vane.

An embodiment of a turning vane also functioning as a heat exchanger disposed in the U-bend portion of a raceway pond bioreactor is shown in FIG. 8. An inlet fluid conduit 810 and an outlet fluid conduit 812 are in fluid communication with the heat exchanger turning vane 803 that comprises an internal cavity for circulating a heat exchange fluid. The inlet fluid conduit 810 comprises a valve 811 for controlling the flow of heat exchange fluid. The heat exchanger turning vane 803 is disposed between the outer wall 801 and the center wall 802 in the same manner as a conventional turning vane.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A mixotrophic bioreactor system, comprising:
  a. An open raceway pond comprising:
      i. An inner volume;
      ii. Two straight away portions separated by a center wall and bounded by straight outer walls and a floor; and
      iii. Two U-bend portions connecting the two straight away portions to form a continuous looped flow path, and bounded by a curved outer wall and a floor;
      iv. Wherein the inner volume has a consistent depth along the entire looped flow path;
  b. At least one submersible thruster disposed within the inner volume a distance from the floor, wherein the at least one thruster is positioned at a U-bend exit and configured to maximize thrust in a straight line flow of an aqueous liquid culture through the straight away portions and add momentum to the aqueous liquid culture along the looped flow path as it exits the U-bend portions of the looped flow path where some velocity of the aqueous liquid culture may be lost due to change in flow direction;
  c. At least one support structure coupled to at least one of the center wall and an outer wall, the support structure suspending the at least one submersible thruster from above at a position within the inner volume of the open raceway pond, wherein the at least one support structure is configured to allow adjustment of the position of the at least one submersible thruster vertically, horizontally, or both; and comprising a distance from the floor to the at least one submersible thruster of 10-50% of a height of an aqueous liquid culture volume in the inner volume of the open raceway pond; and
  d. At least one organic carbon delivery device comprising a pH auxostat system with an outlet positioned to deliver an organic carbon source to the inner volume of the open raceway pond.

2. The mixotrophic bioreactor system of claim 1, wherein the at least one thruster comprises multiple submersible thrusters and the thrusters are disposed within 20% of the U-bend end of the straight away portions.

3. The mixotrophic bioreactor system of claim 2, wherein the width of the open raceway pond is 3 to 12 meters.

4. The mixotrophic bioreactor system of claim 2, wherein the system comprises a culture of microalgae selected from the group consisting of *Chlorella, Thraustochytrids*, and combinations thereof.

5. The mixotrophic bioreactor system of claim 4, wherein the culture has a dissolved oxygen concentration that varies by 10% or less throughout the culture.

6. The mixotrophic bioreactor system of claim 1, wherein the at least one submersible thruster comprises multiple submersible thrusters positioned parallel to each other within the inner volume of the open raceway pond.

7. The mixotrophic bioreactor system of claim 1, wherein the at least one submersible thruster comprises multiple submersible thrusters positioned in a staggered arrangement with relation to each other within the inner volume of the open raceway pond.

8. The mixotrophic bioreactor system of claim 1, wherein the at least one submersible thruster comprises multiple submersible thrusters positioned at spaced intervals within the inner volume of the open raceway pond.

9. The mixotrophic bioreactor system of claim 1, wherein the at least one submersible thruster is disposed between the center wall and the outer wall of at least one of the straight away portions.

10. The mixotrophic bioreactor system of claim 1, wherein the at least one submersible thruster is oriented to circulate a fluid medium through the continuous loop of the open raceway pond.

11. The mixotrophic bioreactor system of claim 1, further comprising at least one heat exchanger.

12. The mixotrophic bioreactor system of claim 11, wherein the at least one heat exchanger is disposed within at least one from the group consisting of the outer walls, the center wall, the floor, and under the floor of the open raceway pond.

13. The mixotrophic bioreactor system of claim 1, further comprising a cover over at least part of the open raceway pond.

14. The mixotrophic bioreactor system of claim 1, further comprising at least one light source selected from the group consisting of natural light and an artificial lighting device.

15. The mixotrophic bioreactor system of claim 1, further comprising at least one arched turning vane disposed within each U-bend portion.

16. The mixotrophic bioreactor system of claim 15, wherein the at least one arched turning vane comprises a symmetrical or asymmetrical curve profile.

17. A mixotrophic bioreactor system, comprising:
  a. An open raceway pond comprising:
    i. A floor;
    ii. Two straight away portions separated by a center wall and bounded by straight outer walls and the floor; and
    iii. Two U-bend portions connecting the two straight away portions to form a continuous looped flow path, and bounded by a curved outer wall and the floor;
    iv. Wherein the floor is flat to create an inner volume that has a consistent depth along the entire looped flow path;
  b. At least one submersible thruster disposed within the inner volume a distance from the floor, wherein the at least one thruster is positioned at a U-bend exit and configured to maximize thrust in a straight line flow of an aqueous liquid culture through the straight away portions and add momentum to the aqueous liquid culture along the looped flow path as it exits the U-bend portions of the looped flow path where some velocity of the aqueous liquid culture may be lost due to change in flow direction;
  c. At least one support structure coupled to at least one of the center wall and an outer wall, the support structure suspending the at least one submersible thruster from above at a position within the inner volume of the open raceway pond wherein the at least one support structure is configured to allow adjustment of the position of the at least one submersible thruster vertically, horizontally, or both; and comprising a distance from the floor to the at least one submersible thruster of 10-50% of a height of an aqueous liquid culture volume in the inner volume of the open raceway pond; and
  d. At least one organic carbon delivery device comprising a pH auxostat system with an outlet positioned to deliver an organic carbon source to the inner volume of the open raceway pond.

* * * * *